US012567340B2

(12) United States Patent
Kokozidis

(10) Patent No.: US 12,567,340 B2
(45) Date of Patent: Mar. 3, 2026

(54) PERSONALIZED LECTURE GENERATOR

(71) Applicant: BIC Violex Single Member S.A., Anoixi (GR)

(72) Inventor: Michail Kokozidis, Anoixi (GR)

(73) Assignee: BIC Violex Single Member S.A., Anoixi (GR)

( * ) Notice: Subject to any disclaimer, the term of this patent is extended or adjusted under 35 U.S.C. 154(b) by 544 days.

(21) Appl. No.: 18/068,447

(22) Filed: Dec. 19, 2022

(65) Prior Publication Data
US 2023/0196936 A1 Jun. 22, 2023

(30) Foreign Application Priority Data
Dec. 20, 2021 (EP) ..................................... 21215946

(51) Int. Cl.
| | |
|---|---|
| *G09B 5/14* | (2006.01) |
| *A61B 5/0531* | (2021.01) |
| *A61B 5/16* | (2006.01) |
| *G06N 3/0475* | (2023.01) |
| *G08B 6/00* | (2006.01) |
| *G09B 5/06* | (2006.01) |

(52) U.S. Cl.
CPC .............. *G09B 5/14* (2013.01); *A61B 5/0531* (2013.01); *A61B 5/165* (2013.01); *G06N 3/0475* (2023.01); *G08B 6/00* (2013.01); *G09B 5/06* (2013.01)

(58) Field of Classification Search
CPC . G09B 5/04; G09B 3/02; G09B 19/00; G09B 5/06; G09B 7/00; G09B 7/04; A61B 5/0533; A61B 5/165
See application file for complete search history.

(56) References Cited

U.S. PATENT DOCUMENTS

| | | |
|---|---|---|
| 10,573,313 B2 | 2/2020 | Mishra et al. |
| 2011/0263946 A1 | 10/2011 | Kaliouby et al. |
| 2013/0245396 A1 | 9/2013 | Berman et al. |
| 2014/0006326 A1* | 1/2014 | Bazanov .................. G06N 5/02 |
| | | 706/46 |

(Continued)

FOREIGN PATENT DOCUMENTS

| | | |
|---|---|---|
| CN | 107085468 A | 8/2017 |
| EP | 2004423 A1 | 12/2008 |

(Continued)

OTHER PUBLICATIONS

"Electrodermal: BIOPAC." BIOPAC Systems, Inc., BIOPAC Systems, Inc., https://www.biopac.com/product-category/education/transducers-education/electrodermal/.

(Continued)

*Primary Examiner* — Jerry-Daryl Fletcher
(74) *Attorney, Agent, or Firm* — Bookoff McAndrews, PLLC

(57) ABSTRACT

In a first aspect, the present disclosure relates to a computer-implemented method for generating a personalized lecture for a user. The method comprises obtaining at least one time series of electrodermal activity data of a user from a sensor and identifying a mental state of the user based on the at least one time series of electrodermal activity data. The method further comprises obtaining teaching content and generating a personalized lecture based on the mental state and the teaching content.

20 Claims, 3 Drawing Sheets

(56) References Cited

U.S. PATENT DOCUMENTS

| | | | |
|---|---|---|---|
| 2014/0336473 A1* | 11/2014 | Greco | A61B 5/7225 |
| | | | 600/509 |
| 2015/0201846 A1 | 7/2015 | Maiershon et al. | |
| 2018/0018540 A1 | 1/2018 | Hazur et al. | |
| 2019/0082990 A1 | 3/2019 | Poltorak | |
| 2019/0133510 A1 | 5/2019 | Kaliouby et al. | |
| 2019/0139428 A1* | 5/2019 | Hatton | G09B 19/00 |
| 2019/0282155 A1 | 9/2019 | Amant et al. | |
| 2020/0178876 A1 | 6/2020 | Lam | |
| 2021/0157402 A1 | 5/2021 | Parshionikar | |

FOREIGN PATENT DOCUMENTS

| | | | |
|---|---|---|---|
| EP | 2730223 A1 | 5/2014 |
| WO | 2011045422 A1 | 4/2011 |

OTHER PUBLICATIONS

European Search Report issued on May 19, 2022 in counterpart European Patent Application No. 21215946.1 (10 bages, in English).

Lee, Taehee. "Pen-Type Electrodermal Activity Sensing System for Stress Detection Based on Likelihood Ratios." Kansas State University, 2020.

* cited by examiner

PERSONALIZED LECTURE GENERATOR

This application claims priority from the European patent application EP21215946.1, filed on Dec. 20, 2021, the entire content of which being incorporated herein by reference.

TECHNICAL FIELD

The present disclosure relates to the field of automated personalized lecture generators. In particular, the present disclosure relates to methods for generating a personalized lecture based on a teaching content and user's mental state.

BACKGROUND

A lecture is an oral presentation intended to present information, a teaching content, to people, e.g. students, about a particular subject. For example, a lecture may be given by a lecturer in the setting of a school or a university. The students are intended to acquire knowledge of the teaching content through the lecture. Studies have shown that the acquisition of knowledge of students from a lecture depends on the mental state of the student. In particular a student may be attentive or inattentive. An inattentive student will typically acquire less knowledge from a lecture compared to an attentive student. However, typically students are attentive for a portion of the lecture and inattentive for another portion of the lecture. In particular, phases of attentiveness and inattentiveness may alternate during a lecture, for example multiple times during one hour. The student may therefore acquire only knowledge of certain teaching contents when attentive during the lecture and miss other teaching contents. However, it may be inefficient for the student to reiterate the entire lecture, for example rewatching the entirety of an online lecture.

Furthermore, the students mental state may indicate how well he as understood the lecture. A student with a confident mental state may have understood a lecture or teaching content comprehensively. A student with an insecure mental state may indicate that a student has not fully comprehended a lecture or teaching content. Additionally, it has been found that mental states may be determined by measuring electrodermal activity, in particular the electrodermal activity of the fingers.

The present disclosure aims to address the aforementioned issues of increasing provision of knowledge in the form of teaching content to students.

SUMMARY

In a first aspect, the present disclosure relates to a computer-implemented method 100 for generating a personalized lecture for a user. The method 100 comprises obtaining 110 at least one time series of electrodermal activity data of a user from a sensor 12 and identifying 120 a mental state of the user based on the at least one time series of electrodermal activity data. The method 100 further comprises obtaining 130 a teaching content and generating 140 a personalized lecture based on the mental state and the teaching content.

The computer implemented method 100 according to the first aspect may improve providing the teaching content to a user. In some embodiments, the user may be a student. The user may listen to or watch a lecture while at least one time series of electrodermal activity data is obtained 110 from the user by the sensor 12. Based on the obtained 110 at least one electrodermal activity data, the user's mental state while listening to the lecture may be identified. Further, the method 100 comprises obtaining 130 the teaching content. The teaching content may be obtained 130 for example by the lecturer entering the teaching content into a device connected to a system executing the method 100. Based on the mental state and the teaching content a personalized lecture may be generated 140. For example, the electrodermal activity data may show that a user was in an inattentive and/or insecure mental state for some time during the lecture and obtain 130 the teaching content for that time. Based on the obtained 130 teaching content and the identified 120 mental state the method may generate 140 a personalized lecture based on for example sequences of the lecture or generative algorithms generating a new lecture, to improve the user's understanding of the teaching content.

The term "teaching content" within this disclosure is well known and attributed its common meaning in this technical field. In some embodiments, the term "teaching content" may refer to the body of knowledge and information that lecturers teach and that students are expected to learn in a given subject or content area. Examples of teaching content may be a language, arts, mathematics, science, or social studies. In some embodiments, the term "teaching content" may refer to facts, concepts, theories, and principles related to a scientific field. In some embodiments, the "teaching content" may be predefined by the user, the lecturer and/or a third party.

The term "mental state" within this disclosure is well known and attributed its common meaning in the technical field. In some embodiments, the term "mental state" may relate to the state of mind of a person, for example, perception, pain experience, belief, desire, intention, emotion, and memory. In some embodiments, the term "mental state" may relate to the degree of attentiveness of a person. In some embodiments, the term "attentiveness" may be used synonymously with the term "focused". The term "inattentive" may refer to the absence of attention.

In embodiments, the at least one time series of electrodermal activity data may be captured by the sensor 12 configured to measure the electric conductivity of skin. The term "electrodermal data" within this disclosure is well known and attributed its common meaning in the technical field. In some embodiments, the term "electrodermal data" may refer to data on the variation of electric conductivity of the skin.

In embodiments, the sensor 12 may be comprised within a writing instrument 10.

In embodiments, the at least one time series of electrodermal activity data may comprise at least one time series of a skin conductance level and/or a electrodermal responses.

In embodiments, obtaining 130 the teaching content may comprise capturing at least one time series of audio data by a microphone 18.

In embodiments, the at least one microphone 18 may be comprised within a writing instrument 10.

In embodiments, obtaining the teaching content may comprise a user, in particular the lecturer, entering the teaching content into a receiver.

In embodiments, the at least one time series of audio data may be interpretable in terms of a natural language.

In embodiments, the at least one time series of audio data may be interpreted into alphanumerical form, in particular string-form, to generate a time series of alphanumerical data.

In embodiments, obtaining 130 the teaching content may comprise a teaching content identification algorithm.

In embodiments, the teaching content identification algorithm may comprise a determination of at least one text module of the at least one time series of alphanumerical data. The alphanumerical data may be N-grams, in particular bi-grams, Noun phrases, themes and/or facets. The teaching content identification algorithm may further comprise obtaining 130 the teaching content conveyed by comparing the at least one text module to predetermined text modules.

In embodiments, obtaining 130 the teaching content based on the at least one time series of data may comprise applying a teaching content recognition algorithm configured to compare the one or more time series of audio data or alphanumerical data, or one or more portions thereof, to predetermined time series of data related to predetermined teaching contents, or portions thereof.

In embodiments, the predetermined text modules, may be queried from a teaching content database.

In embodiments, generating 140 the personalized lecture may comprise applying a personalized lecture content creation algorithm configured to generate 140 a personalized lecture content based on the teaching content.

In embodiments, the personalized lecture content creation algorithm may comprise querying a lecture content database based on the teaching content, in particular querying a lecture content database based on the teaching content to obtain data related to a teaching content.

In embodiments, the personalized content creation algorithm may comprise processing the teaching content or data related to a teaching content by an autoregressive language model, more specifically an autoregressive language model using deep learning, in particular a generative pre-trained transformer 3.

In embodiments, the personalized lecture may comprise a personalized lecture audio sequence based on the personalized lecture content, in particular a personalized lecture audio sequence of a lecturer based on the personalized lecture content.

In embodiments, the personalized audio sequence may be generated by a text to speech system, in particular a text to speech system using audio data of speech by the lecturer.

In embodiments, the personalized audio sequence may be based on the at least one time series of audio data or portions thereof.

In embodiments, the personalized lecture may comprise a personalized lecture video sequence, wherein the personalized lecture video sequence may comprise a mouth performing a series of mouth movements 155 based on the personalized lecture audio sequence, in particular a mouth of the lecturer performing a series of mouth movements based on the personalized lecture audio sequence of the lecturer.

In embodiments, the personalized video sequence may be generated by a neural network, more specifically a generative adversarial network framework, and in particular a generative adversarial network framework using one or more prior video sequences of the lecturer.

In embodiments, the series of mouth movements may be generated by a neural network, more specifically a generative adversarial network framework and in particular a generative adversarial network framework using one or more prior video sequences of the lecturer.

In embodiments, the series of mouth movements may be generated based on at least one prior series of mouth movements by a person, in particular the lecturer, in particular wherein the series of mouth movements may be generated based on at least one prior series of mouth movements by a person, in particular the lecturer, and a related audio sequence expressed by the person.

In embodiments, the personalized lecture video sequence may be based on a video recording of the lecturer, in particular a video recording of the lecturer captured at the same time as the at least one time series of audio data.

In embodiments, the at least one time series of electrodermal activity data may be obtained by measuring a skin conductance in an interval between about 0.1 Hz to about 100 Hz, more specifically between about 1 Hz to about 20 Hz and in particular between about 1 Hz to about 10 Hz.

In embodiments, the skin conductance level may be the floating average of the skin conductance over a time period between about 10 s to about 60 minutes, more specifically between about 2 minutes to about 20 minutes and in particular between about 5 minutes to about 10 minutes.

In embodiments, identifying 120 the user's mental state based on the at least one time series of electrodermal activity data may comprise applying a mental state recognition algorithm.

In embodiments, the mental state recognition algorithm may be configured to compare the one or more time series of electrodermal activity data, or one or more portions thereof, to one or more threshold values.

In embodiments, the mental state recognition algorithm may comprise applying a through-to-peak technique and/or a continuous decomposition analysis on the at least one time series of electrodermal activity data.

In embodiments, the mental state recognition algorithm may be configured to compare the at least one time series of electrodermal activity data, or one or more portions thereof, to predetermined time series of electrodermal activity data related to predetermined mental states, or portions thereof.

In embodiments, the mental state recognition algorithm may comprise processing the at least one time series of electrodermal activity data by a neural network, in particular a neural network including one or more recurrent neural networks, more particularly a neural network including one or more long-short term memory neural network.

In embodiments, the mental state may correspond to at least one of a plurality of predefined mental states.

In embodiments, the identified 120 mental state may be an attentiveness, confidence, boredom, anxiety and/or sadness.

In embodiments, the identified 120 mental state may be quantified, more specifically wherein the identified mental state may be ranked into tiers, and in particular wherein the identified mental state may be ranked into tiers from a low tier to a high tier.

In embodiments, a personalized lecture may be generated depending on the identified 120 mental state.

In embodiments, the identified 120 mental state may be a lack of attentiveness, in particular a low tier of attentiveness.

In embodiments, the identified 120 mental state may be a lack of confidence, in particular a low tier of confidence and/or wherein the identified 120 mental state may be a high degree of confidence, in particular a high tier of confidence.

In embodiments, an alertness signal may be generated depending on the identified 120 mental state, more specifically when a lack of attentiveness may be identified, in particular when a low tier of attentiveness may be identified.

In a second aspect, the present disclosure relates to a computer system 300 configured to execute the computer-implemented method 100 according to any preceding embodiment.

In embodiments, the computer system 300 may comprise a writing instrument 10, wherein the writing instrument comprises a sensor 12 configured to measure the electric conductivity of skin and a first interface 14. The computer system 300 further comprises a processing unit 20 remote from the writing instrument, wherein the processing unit 20 comprises a second interface 22. The first 14 and second interface 22 are configured to exchange data.

In embodiments, the first interface 14 is configured to send the at least one time series of electrodermal activity data to the second interface 22.

In embodiments, the second interface is configured to send a notification that a personalized lecture is available to the first interface 14.

In a third aspect, the present disclosure relates to a writing instrument 10 comprising a sensor 12 configured to measure the electric conductivity of skin and a first interface 14 configured to communicate with a second interface 22.

In embodiments, the writing instrument 10 comprises a signaler, in particular a vibrating alert configured to activate when receiving the alertness signal.

In a fourth aspect, the present disclosure relates to a non-transitory computer-readable medium 400 characterized by a processor configured to execute the computer-implemented method 100 according to any preceding embodiment.

DETAILED DESCRIPTION

Figure 1:
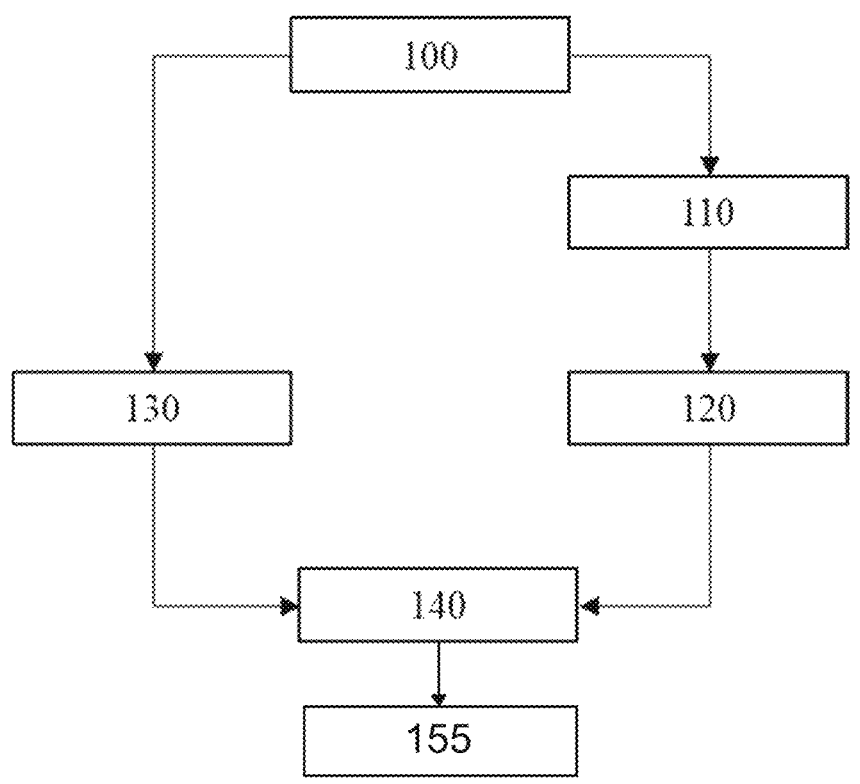
FIG. 1 shows the method 100 according to an embodiment of the present disclosure.

Hereinafter, a detailed description will be given of the present disclosure. The terms or words used in the description and the aspects of the present disclosure are not to be construed limitedly as only having common-language or dictionary meanings and should, unless specifically defined otherwise in the following description, be interpreted as having their ordinary technical meaning as established in the relevant technical field. The detailed description will refer to specific embodiments to better illustrate the present disclosure, however, it should be understood that the presented disclosure is not limited to these specific embodiments.

Studies have shown that the acquisition of knowledge of students from a lecture depends on the mental state of the student. In particular a student may be attentive or inattentive.

Furthermore, the students mental state may indicate how well he as understood the lecture. A student with a confident mental state may have understood a lecture or teaching content comprehensively. A student with an insecure mental state may indicate that a student has not fully comprehended a lecture or teaching content.

Further, it has been found that mental states may be determined by measuring electrodermal activity, in particular the electrodermal activity of the fingers.

In a first aspect, the present disclosure relates to a computer-implemented method 100 for generating a personalized lecture for a user. The method 100 comprises obtaining 110 at least one time series of electrodermal activity data of a user from a sensor 12 and identifying 120 a mental state of the user based on the at least one time series of electrodermal activity data. The method 100 further comprises obtaining 130 a teaching content and generating 140 a personalized lecture based on the mental state and the teaching content.

The computer implemented method 100 according to the first aspect may improve providing the teaching content to a user. An exemplary embodiment of the method 100 according to the first aspect is presented in FIG. 1. In some embodiments, the user may be a student. The user may listen to or watch a lecture while at least one time series of electrodermal activity data is obtained 110 from the user by the sensor 12. Based on the obtained 110 at least one electrodermal activity data, the user's mental state while listening to the lecture may be identified. Further, the method 100 comprises obtaining 130 the teaching content. The teaching content may be obtained 130 for example by the lecturer entering the teaching content into a device connected to a system executing the method 100. Based on the mental state and the teaching content a personalized lecture may be generated 140. For example, the electrodermal activity data may show that a user was in an inattentive and/or insecure mental state for some time during the lecture and obtain 130 the teaching content for that time. Based on the obtained 130 teaching content and the identified mental 120 state the method may generate 140 a personalized lecture based on for example sequences of the lecture or generative algorithms generating a new lecture, to improve the user's understanding of the teaching content.

The term "teaching content" within this disclosure is well known and attributed its common meaning in this technical field. In some embodiments, the term "teaching content" may refer to the body of knowledge and information that lecturers teach and that students are expected to learn in a given subject or content area. Examples of teaching content may be English language arts, mathematics, science, or social studies. In some embodiments, the term "teaching content" may refer to facts, concepts, theories, and principles related to a scientific field. In some embodiments, the "teaching content" may be predefined by the user and/or a third party.

The term "mental state" within this disclosure is well known and attributed its common meaning in the technical field. In some embodiments, the term "mental state" may relate to the state of mind of a person, for example, perception, pain experience, belief, desire, intention, emotion, and memory. In some embodiments, the term "mental state" may relate to the degree of attentiveness of a person. In some embodiments, the term "attentiveness" may be used synonymously with the term "focused". The term "inattentive" may refer to the absence of attention.

In some embodiments, the at least one time series of electrodermal activity data may be captured by the sensor 12 configured to measure the electric conductivity of skin. The term "electrodermal data" within this disclosure is well known and attributed its common meaning in the technical field. In some embodiments, the term "electrodermal data" may refer to data on the variation of electric conductivity of the skin. The electric conductivity of the skin may vary involuntary, in particular due to emotional arousal and sympathetic activity. The emotional arousal and sympathetic activity, which may also relate to a user's mental state, may lead to the release of sweat, by sweat glands comprised within the user's skin. The sweat comprising water and salts may have a higher electric conductivity than dry skin and may therefore increase the electric conductivity of the user's skin. Hence, a change in the mental state is typically related to a change in electric conductivity of the skin. Tracking electrodermal activity data is already used for example in polygraphs or lie detector tests.

It is known that identifying a mental state may be the most precise when based on the electrodermal activity of the fingers. In some embodiments, the sensor 12 may be comprised within a writing instrument 10. In that way, a user will commonly automatically use a writing instrument with his fingers. Hence, the most precise electrodermal activity data can be obtained through a writing instrument 10 during normal use. Further, the user may require the writing instrument 10 anyways for e.g. taking notes. As a result, the user may not be required to carry around or use a dedicated device to profit of the method 100. Further, the writing instrument may obtain 110 the electrodermal activity data in real time.

In some embodiments, the at least one time series of electrodermal activity data may comprise at least one time series of a skin conductance level and/or electrodermal responses. The electrodermal activity may comprise two components. The skin conductance level may be a baseline, in particular a baseline to which the electric conductivity of the skin falls if the user has a mental state which does not lead to a rapid increase in electroconductivity of the skin. The skin conductance level may only change slowly over time. The skin conductance level may be regarded as the slow varying tonic sympathetic activity. The electrodermal response may be a fast variation in skin conductance. The electrodermal response may be regarded as the fast varying phasic sympathetic activity. When plotting electrodermal activity the electrodermal response may be seen as peaks emerging from a baseline. The analysis of the electrodermal response or skin conductance level and in particular the analysis of the electrodermal response together with skin conductance level may allow identifying the user's mental state.

In some embodiments, obtaining the teaching content may comprise a user, in particular the lecturer, entering the teaching content into a receiver. For example, the teaching content may be entered by the user and/or the lecturer into a receiver, such as a mobile phone app or computer. For example, the lecturer into the receiver in 5 minute intervals. When a specific mental state, e.g. inattentiveness, is identified 120 the obtained 130 teaching content is saved and used to generate 140 the personalized lecture. A plurality of obtained 130 teaching contents may be grouped to generate 140 the personalized lecture. The teaching content may then be provided by an interface to a system executing the method 100. The teaching content may be defined broadly, e.g. computer science, or more specific, e.g. speech analysis algorithms.

In some embodiments, obtaining 130 the teaching content may comprise capturing at least one time series of audio data by a microphone 18. The at least one time series of audio data may be used to obtain 130 the teaching content. Additionally or alternatively, the at least one time series of audio data may be for example stored and made available to the user to replay at a later time. In some embodiments, the storage of the at least one time series of audio data may also be regarded as obtaining 130 a teaching content. For example, the method 100 may comprise identifying 120 that the user's mental state is inattentive and start recording and/or storing the at least one time series of audio data. After the lecture the method 100 may present the user with the information that at least one time series of audio data has been stored for replay. The information that at least one time series of audio data has been stored for replay may be indicated to the user for example through a mobile phone app or by a visual indicator 14 on the writing instrument 10. The visual indicator 14 may be for example a light, in particular an LED, which may for example flash when at least one time series of audio data has been stored for replay.

In some embodiments, the at least one microphone 18 may be comprised within a writing instrument 10. With that arrangement, the user may require the writing instrument 10 anyways for e.g. taking notes. As a result, the user may not be required to carry around or use a dedicated device to profit of the method 100. Further, the writing instrument may obtain 110 the electrodermal activity data in real time.

In some embodiments, the at least one time series of audio data may be interpretable in terms of a natural language. The teaching content may be obtained 130 by an automatized process. The time series of audio data captured by the microphone 18 may be evaluated by additional steps of the method 100 to obtain 130 the teaching content. These additional steps may require or be facilitated by the at least one time series of audio data being interpretable in terms of a natural language.

In some embodiments, the at least one time series of audio data may be interpreted into alphanumerical form, in particular string-form, to generate a time series of alphanumerical data. The time series of alphanumerical data may be more efficiently processable by a computer.

In some embodiments, obtaining 130 the teaching content may comprise a teaching content identification algorithm.

In some embodiments, the teaching content identification algorithm may comprise a determination of at least one text module of the at least one time series of alphanumerical data. The alphanumerical data may be N-grams, in particular bi-grams, Noun phrases, themes and/or facets. The teaching content identification algorithm may further comprise obtaining 130 the teaching content conveyed by comparing the at least one text module to predetermined text modules. N-grams, in particular bi-grams, Noun phrases, themes and/or facets may allow precise and/or computationally efficient identification of the teaching content. For example, the exemplary time series may comprise the sentence "Hannibal of Carthage crossed the alps with elephants". From the sentence the bi-grams "Hannibal Carthage" and "Alps Elephants" may be extracted through the teaching content identification algorithm. Based on the bi-grams the teaching content may be obtained 130 as "second Punic war" and/or "Hannibal's crossing of the Alps".

In some embodiments, obtaining 130 the teaching content based on the at least one time series of audio data may comprise applying a teaching content recognition algorithm configured to compare the one or more time series of audio data or alphanumerical data, or one or more portions thereof, to predetermined time series of data related to predetermined teaching contents, or portions thereof. For example, a one minute long time series of audio data or the respective time series of alphanumerical data corresponding to the audio data may be used to obtain 130 the teaching content. The exemplary time series may comprise the sentence "Hannibal of Carthage crossed the alps with elephants". The sentence itself or the word combination "elephant", "Carthage", "Hannibal" and "alps" may be compared to predetermined sentences or word combinations of predetermined teaching contents, or portions thereof which may allow to obtain 130 the teaching content "second Punic war" and/or "Hannibal's crossing of the Alps". For example, in use, when a specific mental state, e.g. inattentiveness, is identified 120 the obtained 130 teaching content is saved and used to generate 140 the personalized lecture. A plurality of obtained 130 teaching contents may be grouped to generate 140 the personalized lecture.

In some embodiments, the predetermined text modules, may be queried from a teaching content database. In some embodiments, the "teaching content" may be predefined by the user, the lecturer or a third party, e.g. the Ministry of Education and the Arts.

In some embodiments, generating 140 the personalized lecture may comprise applying a personalized lecture content creation algorithm configured to generate a personalized lecture content based on the teaching content. The personalized lecture content may allow providing the user not only with a recording of the lecturer to replay. Instead, the personalized lecture content creation content algorithm may provide the user with a personalized lecture adapted to his needs, which may improve his studying efficiency. This may also allow providing users which have shown a confident mental state during the lecture with additional teaching content to deepen or expand their understanding.

In some embodiments, the personalized lecture content creation algorithm may comprise querying a lecture content database based on the teaching content, in particular querying a lecture content database based on the teaching content to obtain data related to a teaching content. For example, the personalized lecture content creation algorithm may query a predetermined text from the database. For example, a repetition unit or extensive knowledge on Hannibal Crossing the Alps.

In some embodiments, the personalized content creation algorithm may comprise processing the teaching content or data related to a teaching content by an autoregressive language model, more specifically an autoregressive language model using deep learning, in particular a generative pre-trained transformer 3. The autoregressive language model may create a personalized lecture content based on one or more teaching contents obtained 130. The autoregressive language model may for example create text including only the parts of the lecture or teaching contents where the user was inattentive. The autoregressive language model may be trained and tested with predetermined texts for defined teaching contents.

In some embodiments, the personalized lecture may comprise a personalized lecture audio sequence based on the personalized lecture content, in particular a personalized lecture audio sequence of a lecturer based on the personalized lecture content.

In some embodiments, the personalized audio sequence may be generated by a text to speech system, in particular a text to speech system using audio data of speech by the lecturer. The text to speech system may create an audio sequence of the personalized lecture content for the user to listen to. The text may have been previously generated by the autoregressive language model. A personalized lecture audio sequence may improve the users understanding of the teaching content compared to a personalized lecture content in written form.

In some embodiments, the personalized audio sequence may be based on the at least one time series of audio data or portions thereof. As mentioned above, the personalized lecture audio sequence may also be a recording of the lecturer, for example a recording of the lecturer when it has been identified 120 that the user was inattentive. A personalized audio sequence only comprising the at least one time series of audio or portions thereof where the student was inattentive may improve the studying efficiency of the student, as the user does not need to relisten to parts where the user was already attentive.

Further, studies have shown that seeing a person speaking, more specifically the mouth movements of a person speaking, can improve speech perception. Improved speech perception may lead to improved teaching efficiency.

Hence, in some embodiments, the personalized lecture may comprise a personalized lecture video sequence, wherein the personalized lecture video sequence may comprise a mouth performing a series of mouth movements 155 based on the personalized lecture audio sequence, in particular a mouth of the lecturer performing a series of mouth movements based on the personalized lecture audio sequence of the lecturer. The personalized video sequence, in particular a personalized video sequence comprising mouth movements 155 which are based on an audio sequence of the personalized lecture may improve the user's speech perception and thereby the user's learning success.

In some embodiments, the personalized video sequence may be generated by a neural network, more specifically a generative adversarial network framework, and in particular a generative adversarial network framework using one or more prior video sequences of the lecturer. The neural network may be trained with predetermined audio sequences for which the original video sequence, in particular the original mouth movements, are available. For example, a lecturer may purposely provide the neural network with audio and video sequences of himself. The neural network may also be trained by third person with a standardized set of audio sequences correlated to video sequences, in particular mouth movements. Hence, the neural network may be trained with known audio data—video sequence pairs. Subsequently, the neural network may be tested by providing it only with audio sequences and controlling whether the neural network generates acceptable video sequences. The neural network may test itself by analyzing the difference between the generated video sequence and the original video sequence. The neural network generating 140 the personalized video sequence may allow providing the student with a complete personalized lecture, for example by having a text generated by an autoregressive language model, which is additionally processed into one or more audio sequences and based on the one or more audio sequences one or more video sequences are generated to attain a complete personalized lecture for the user.

In some embodiments, the series of mouth movements may be generated by a neural network, more specifically a generative adversarial network framework and in particular a generative adversarial network framework using one or more prior video sequences of the lecturer. The mouth movements may be the most important for improving the user's speech perception. Further, the mouth movements may be fitted to a video of the lecturer to replace the original mouth movements of lecturer with those fitting to the personalized lecture audio sequence. A neural network only generating mouth movements may require less computing power and time.

In some embodiments, the series of mouth movements may be generated based on at least one prior series of mouth movements by a person, in particular the lecturer, in particular wherein the series of mouth movements may be generated based on at least one prior series of mouth movements by a person, in particular the lecturer, and a related audio sequence expressed by the person.

In some embodiments, the personalized lecture video sequence may be based on a video recording of the lecturer, in particular a video recording of the lecturer captured at the same time as the at least one time series of audio data. The personalized lecture video sequence may also be a video of the lecturer, for example a video of the lecturer when it has been identified 120 that the user was inattentive. The video sequence may be obtained by an additional camera. Additionally or alternatively, the video sequence may also be obtained by storing an online lecture by the lecturer. Many classes are nowadays held as online lectures, which are provided to users including a video and audio sequence. The method 100 comprise using these video and audio sequences or parts thereof to generate 140 the personalized lecture.

In some embodiments, the at least one time series of electrodermal activity data may be obtained by measuring a skin conductance in an interval between about 0.1 Hz to about 100 Hz, more specifically between about 1 Hz to about 20 Hz and in particular between about 1 Hz to about 10 Hz. A shorter interval may deliver a more precise measurement but also require a higher computing capacity.

In some embodiments, the skin conductance level may be the floating average of the skin conductance over a time period between about 10 s to about 60 minutes, more specifically between about 2 minute to about 20 minutes and in particular between about 5 minutes to about 10 minutes. A shorter time period may more accurately assess the current skin conductance level, however, a shorter time period may also lead to distortion of the skin conductance level by the electrodermal response.

In some embodiments, identifying 120 the user's mental state based on the at least one time series of electrodermal activity data may comprise applying a mental state recognition algorithm.

In some embodiments, the mental state recognition algorithm may be configured to compare the one or more time series of electrodermal activity data, or one or more portions thereof, to one or more threshold values. For example, values, such as a certain percentual increases of electrodermal activity, hence electrodermal responses, over a certain amount of time may be known to correlate to certain mental states. These values may then be set as threshold values to allow identification 120 of the mental state.

In some embodiments, the mental state recognition algorithm may comprise applying a through-to-peak technique and/or a continuous decomposition analysis on the at least one time series of electrodermal activity data. The trough-to-peak technique and/or continuous decomposition analysis are known in the technical field of electrodermal activity data analysis and are known to more accurately determine the mental state compared to other analysis technologies.

In some embodiments, the mental state recognition algorithm may be configured to compare the at least one time series of electrodermal activity data, or one or more portions thereof, to predetermined time series of electrodermal activity data related to predetermined mental states, or portions thereof. For example, certain percentual increases of electrodermal activity, hence electrodermal responses, over a certain amount of time may be known to correlate to certain mental states. The mental state recognition algorithm may therefore compare the at least one time series electrodermal activity data to predetermined time series of electrodermal activity data related to predetermined mental states to identify 120 the user's mental state.

In some embodiments, the mental state recognition algorithm may comprise processing the at least one time series of electrodermal activity data by a neural network, in particular a neural network including one or more recurrent neural networks, more particularly a neural network including one or more long-short term memory neural network. The neural network may be trained with predetermined time series of electrodermal activity for which the mental state is known. For example, the user or a third party may provide the predetermined time series of electrodermal activity while being questioned which mental state he is currently in. Alternatively or additionally, the mental state may be analyzed by additional measurements. For example, blood tests may be performed in intervals to determine the stress level of a person and this stress level may be subsequently correlated to the predetermined time series of electrodermal activity. In another example, the mental state for the training data may be identified by an electroencephalogram. The neural network may also be trained by a third person with a standardized set of predetermined time series of electrodermal activity correlated to mental states. Hence, the neural network may be trained with known "electrodermal activity—mental state"-pairs. Subsequently, the neural network may be tested by providing it only with predetermined time series of electrodermal activity and controlling whether the neural network identifies 120 the correct mental state. The neural network may also test itself.

In some embodiments, the mental state may correspond to at least one of a plurality of predefined mental states.

In some embodiments, the identified 120 mental state may be an attentiveness, confidence, boredom, anxiety and/or sadness. Additionally or alternatively, the identified 120 mental state may be a belief and/or perception.

In some embodiments, the identified 120 mental state may be quantified, more specifically wherein the identified 120 mental state may be ranked into tiers, and in particular wherein the identified 120 mental state may be ranked into tiers from a low tier to a high tier. For example, there may be high tiers of attentiveness or high tiers of inattentiveness. Alternatively, there may be high tiers of attentiveness and low tiers of attentiveness correspond to inattentiveness. Personalized lectures may only be generated 140 for certain tiers of mental states, for example a high tier of attentiveness to deepen and expand the user's knowledge on a teaching content or a low tier of attentiveness for user to rework on a teaching content he was inattentive to.

In some embodiments, a personalized lecture may be generated depending on the identified 120 mental state.

In some embodiments, the identified 120 mental state may be a lack of attentiveness, in particular a low tier of attentiveness.

In some embodiments, the identified 120 mental state may be a lack of confidence, in particular a low tier of confidence and/or wherein the identified 120 mental state may be a high degree of confidence, in particular a high tier of confidence. As mentioned above, it may be, in some instances, to provide user's which are confident in their knowledge of a teaching content with a personalized lecture to expand or deepen their understanding of the teaching content.

In some embodiments, an alertness signal may be generated depending on the identified 120 mental state, more specifically when a lack of attentiveness may be identified, in particular when a low tier of attentiveness may be identified.

In a second aspect, the present disclosure relates to a computer system 300 configured to execute the computer-implemented method 100 according to any preceding embodiment.

Figure 2:
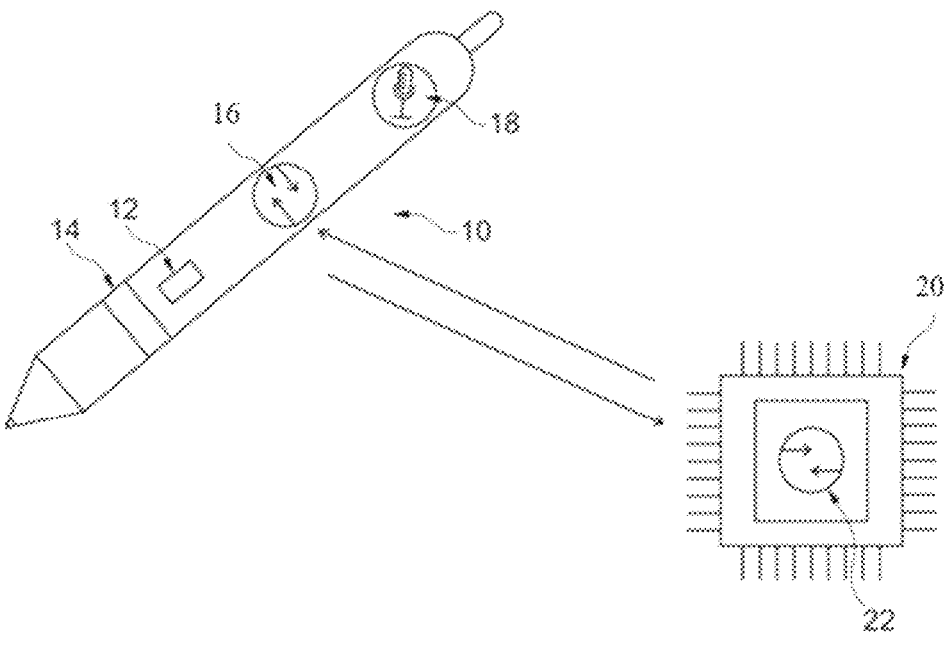
FIG. 2 shows a computer system comprising a processing unit 20 and a writing instrument 10 according to an embodiment of the present disclosure.

FIG. 2 shows exemplary embodiments of the computer system 300. In some embodiments, the computer system 300 may comprise a writing instrument 10, wherein the writing instrument comprises a sensor 12 configured to measure the electric conductivity of skin and a first interface 14. The computer system 300 further comprises a processing unit 20 remote from the writing instrument, wherein the processing unit 20 comprises a second interface 22. The first 16 and second interface 22 are configured to exchange data. In some embodiments, only the first interface 16 may send data to the second interface 22. The exchange of data does not have to be bilateral. As mentioned above, having the sensor 12, the microphone 18 and the visual indicator 14 being comprised within a writing instrument 10, allow the user to require the writing instrument 10 anyways for e.g. taking notes. As a result, the user may not be required to carry around a dedicated device to profit of the method 100.

However, it may be unfeasible and/or impracticable to include the processing unit 20 into the writing instrument, as it may require for example to much space and/or power. Therefore, in some instances, only the first interface 16 may be included into the writing instrument 10, which exchanges data with the second interface 22 of the processing unit 20, as shown in FIG. 2.

For example, the sensor 12 comprised within the writing instrument 10 may obtain the at least one time series of electrodermal activity data and send it to the second interface 22 of the processing unit 20. The processing unit 20 may then identify the mental state. The processing unit 20 may then for example send a signal to the first interface 14 that the microphone 18 comprised within the writing instrument shall start capturing the at least one time series of audio data.

Additionally, in an example, the microphone 18 comprised within the writing instrument 10 may obtain the at least one time series of audio data and send it to the second interface 22 of the processing unit 20. The processing unit 20 may then identify the teaching content, for example by executing the teaching content recognition algorithm. Additionally or alternatively the processing unit 20 may store the at least one time series of audio data. The processing unit 20 may then, for example, send the notice that a personalized lecture is available for the user to the first interface 16 for the writing instrument 10 to present the information to the user via the visual indicator 14.

Additionally, in an example, the microphone 18 comprised within the writing instrument 10 may obtain the at least one time series of audio data and send it to the second interface 22 of the processing unit 20. The processing unit 20 may then identify the teaching content, for example by executing the teaching content recognition algorithm. The processing unit 20 may then for example send the notice that a personalized lecture is available for the user to the first interface 16, for writing instrument 10 to present the information to the user via the visual indicator 14.

In some embodiments, the first interface 14 is configured to send the at least one time series of electrodermal activity data to the second interface 22. In an example, the identification 120 of the mental state may be performed by a processing unit 20 remote of the writing instrument, as the processing unit 20 may require too much space/power.

In some embodiments, the second interface is configured to send a notification that a personalized lecture is available the first interface 14.

In a third aspect, the present disclosure relates to a writing instrument 10 comprising a sensor 12 configured to measure the electric conductivity of skin and a first interface 14 configured to communicate with a second interface 22.

In some embodiments, the writing instrument 10 comprises a signaler, in particular a vibrating alert configured to activate when receiving the alertness signal. The writing instrument comprising a signaler configured to activate when receiving the alertness signal may for example alert the user by vibration or a light, to indicate to the user that he is inattentive. This may improve the attentiveness of the user and thereby the understanding of teaching content by the user.

In a fourth aspect, the present disclosure relates to a non-transitory computer-readable medium 400 characterized by a processor configured to execute the computer-implemented method 100 according to any preceding embodiment.

Figure 3:
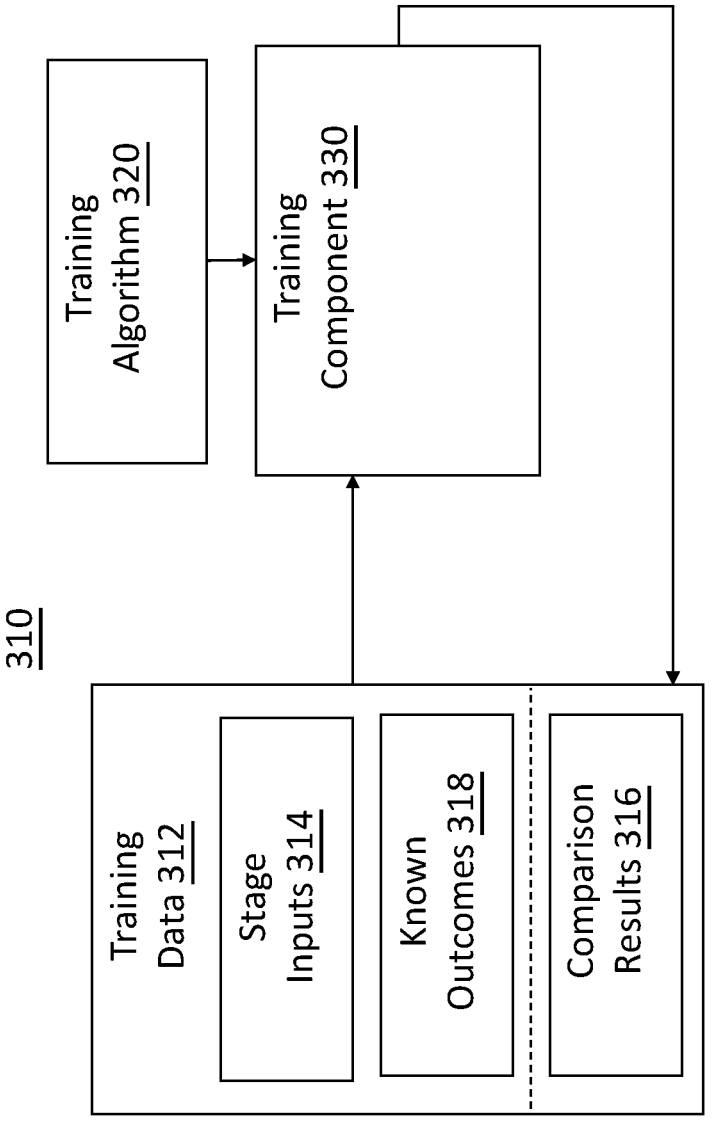
FIG. 3 shows an example machine learning training flow chart.

One or more implementations disclosed herein include and/or may be implemented using a machine learning model. For example, one or more of the lecture or generative algorithms, teaching content identification algorithm, personalized lecture content creation algorithm, mental state recognition algorithm, speech analysis algorithms, teaching content recognition algorithm, may be implemented using a machine learning model and/or may be used to train a machine learning model. A given machine learning model may be trained using the data flow 310 of FIG. 3. Training data 312 may include one or more of stage inputs 314 and known outcomes 318 related to a machine learning model to be trained. The stage inputs 314 may be from any applicable source including text, visual representations, data, values, comparisons, stage outputs (e.g., one or more outputs from FIGS. 1 and/or 2). The known outcomes 318 may be included for machine learning models generated based on supervised or semi-supervised training. An unsupervised machine learning model may not be trained using known outcomes 318. Known outcomes 318 may include known or desired outputs for future inputs similar to or in the same category as stage inputs 314 that do not have corresponding known outputs.

The training data 312 and a training algorithm 320 (e.g., one or more of the lecture or generative algorithms, teaching content identification algorithm, personalized lecture content creation algorithm, mental state recognition algorithm, speech analysis algorithms, teaching content recognition algorithm implemented using a machine learning model and/or may be used to train a machine learning model) may be provided to a training component 330 that may apply the training data 312 to the training algorithm 320 to generate a machine learning model. According to an implementation, the training component 330 may be provided comparison results 316 that compare a previous output of the corresponding machine learning model to apply the previous result to re-train the machine learning model. The comparison results 316 may be used by the training component 330 to update the corresponding machine learning model. The training algorithm 320 may utilize machine learning networks and/or models including, but not limited to a deep learning network such as Deep Neural Networks (DNN), Convolutional Neural Networks (CNN), Fully Convolutional Networks (FCN) and Recurrent Neural Networks (RCN), probabilistic models such as Bayesian Networks and Graphical Models, and/or discriminative models such as Decision Forests and maximum margin methods, or the like.

A machine learning model used herein may be trained and/or used by adjusting one or more weights and/or one or more layers of the machine learning model. For example, during training, a given weight may be adjusted (e.g., increased, decreased, removed) based on training data or input data. Similarly, a layer may be updated, added, or removed based on training data/and or input data. The resulting outputs may be adjusted based on the adjusted weights and/or layers.

In general, any process or operation discussed in this disclosure that is understood to be computer-implementable, such as the process illustrated in FIGS. 1 and/or 2 may be performed by one or more processors of a computer system as described above. A process or process step performed by one or more processors may also be referred to as an operation. The one or more processors may be configured to perform such processes by having access to instructions (e.g., software or computer-readable code) that, when executed by the one or more processors, cause the one or more processors to perform the processes. The instructions may be stored in a memory of the computer system. A processor may be a central processing unit (CPU), a graphics processing unit (GPU), or any suitable types of processing unit.

A computer system, such as a system or device implementing a process or operation in the examples above, may include one or more computing devices. One or more processors of a computer system may be included in a single computing device or distributed among a plurality of computing devices. One or more processors of a computer system may be connected to a data storage device. A memory of the computer system may include the respective memory of each computing device of the plurality of computing devices.

Figure 4:
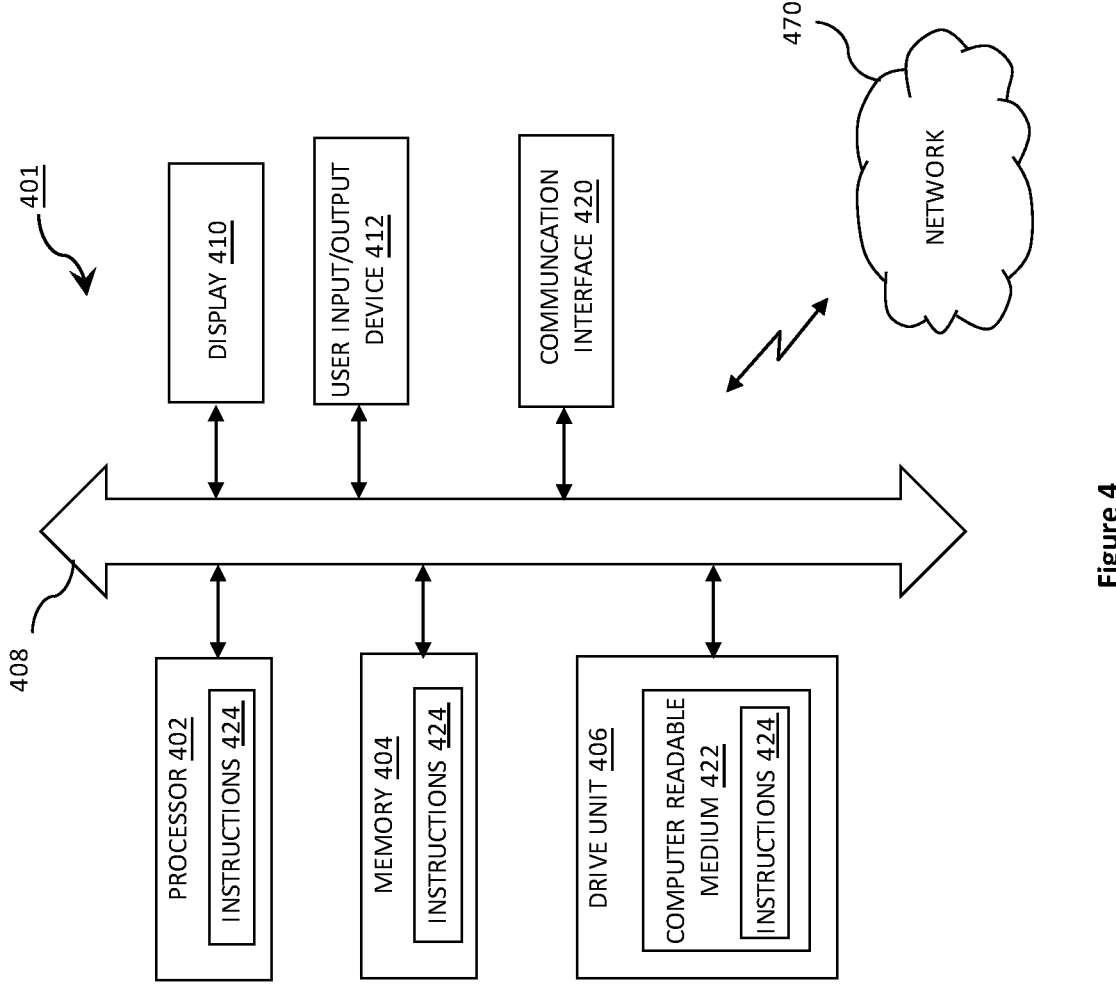
FIG. 4 illustrates an implementation of a computer system that executes techniques presented herein.

In various embodiments, one or more portions of method 100 and system 300 may be implemented in, for instance, a chip set including a processor and a memory as shown in FIG. 4. FIG. 4 illustrates an implementation of a general computer system that may execute techniques presented herein. The computer system 401 can include a set of instructions that can be executed to cause the computer system 401 to perform any one or more of the methods, system, or computer based functions disclosed herein. The computer system 401 may operate as a standalone device or may be connected, e.g., using a network, to other computer systems or peripheral devices.

Unless specifically stated otherwise, as apparent from the following discussions, it is appreciated that throughout the specification, discussions utilizing terms such as "processing," "computing," "determining", or the like, refer to the action and/or processes of a computer or computing system, or similar electronic computing device, that manipulate and/or transform data represented as physical, such as electronic, quantities into other data similarly represented as physical quantities.

In a similar manner, the term "processor" may refer to any device or portion of a device that processes electronic data, e.g., from registers and/or memory to transform that electronic data into other electronic data that, e.g., may be stored in registers and/or memory. A "computer," a "computing machine," a "computing platform," a "computing device," or a "server" may include one or more processors.

In a networked deployment, the computer system 401 may operate in the capacity of a server or as a client user computer in a server-client user network environment, or as a peer computer system in a peer-to-peer (or distributed) network environment. The computer system 401 can also be implemented as or incorporated into various devices, such as a personal computer (PC), a tablet PC, a personal digital assistant (PDA), a mobile device, a palmtop computer, a laptop computer, a desktop computer, a communications device, a wireless telephone, a land-line telephone, a control system, a camera, a scanner, a facsimile machine, a personal trusted device, a web appliance, a network router, switch or bridge, or any other machine capable of executing a set of instructions (sequential or otherwise) that specify actions to be taken by that machine. In a particular implementation, the computer system 401 can be implemented using electronic devices that provide voice, video, or data communication. Further, while a computer system 401 is illustrated as a single system, the term "system" shall also be taken to include any collection of systems or sub-systems that individually or jointly execute a set, or multiple sets, of instructions to perform one or more computer functions.

As illustrated in FIG. 4, the computer system 401 may include a processor 402, e.g., a central processing unit (CPU), a graphics processing unit (GPU), or both. The processor 402 may be a component in a variety of systems. For example, the processor 402 may be part of a standard personal computer or a workstation. The processor 402 may be one or more general processors, digital signal processors, application specific integrated circuits, field programmable gate arrays, servers, networks, digital circuits, analog circuits, combinations thereof, or other now known or later developed devices for analyzing and processing data. The processor 402 may implement a software program, such as code generated manually (i.e., programmed).

The computer system 401 may include a memory 404 that can communicate via a bus 408. The memory 404 may be a main memory, a static memory, or a dynamic memory. The memory 404 may include, but is not limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one implementation, the memory 404 includes a cache or random-access memory for the processor 402. In alternative implementations, the memory 404 is separate from the processor 402, such as a cache memory of a processor, the system memory, or other memory. The memory 404 may be an external storage device or database for storing data. Examples include a hard drive, compact disc ("CD"), digital video disc ("DVD"), memory card, memory stick, floppy disc, universal serial bus ("USB") memory device, or any other device operative to store data. The memory 404 is operable to store instructions executable by the processor 402. The functions, acts or tasks illustrated in the figures or described herein may be performed by the processor 402 executing the instructions stored in the memory 404. The functions, acts or tasks are independent of the particular type of instructions set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

As shown, the computer system 401 may further include a display 410, such as a liquid crystal display (LCD), an organic light emitting diode (OLED), a flat panel display, a solid-state display, a cathode ray tube (CRT), a projector, a printer or other now known or later developed display device for outputting determined information. The display 410 may act as an interface for the user to see the functioning of the processor 402, or specifically as an interface with the software stored in the memory 404 or in the drive unit 406.

Additionally or alternatively, the computer system 401 may include an input/output device 412 configured to allow a user to interact with any of the components of computer system 401. The input/output device 412 may be a number pad, a keyboard, or a cursor control device, such as a mouse, or a joystick, touch screen display, remote control, or any other device operative to interact with the computer system 401.

The computer system 401 may also or alternatively include drive unit 406 implemented as a disk or optical drive. The drive unit 406 may include a computer-readable medium 422 in which one or more sets of instructions 424, e.g. software, can be embedded. Further, instructions 424 may embody one or more of the methods or logic as described herein. The instructions 424 may reside completely or partially within the memory 404 and/or within the processor 402 during execution by the computer system 401. The memory 404 and the processor 402 also may include computer-readable media as discussed above.

In some systems, a computer-readable medium 422 includes instructions 424 or receives and executes instructions 424 responsive to a propagated signal so that a device connected to a network 470 can communicate voice, video, audio, images, or any other data over the network 470. Further, the instructions 424 may be transmitted or received over the network 470 via a communication port or interface 420, and/or using a bus 408. The communication port or interface 420 may be a part of the processor 402 or may be a separate component. The communication port or interface 420 may be created in software or may be a physical connection in hardware. The communication port or interface 420 may be configured to connect with a network 470, external media, the display 410, or any other components in computer system 401, or combinations thereof. The connection with the network 470 may be a physical connection, such as a wired Ethernet connection or may be established wirelessly as discussed below. Likewise, the additional connections with other components of the computer system 401 may be physical connections or may be established wirelessly. The network 470 may alternatively be directly connected to a bus 408.

While the computer-readable medium 422 is shown to be a single medium, the term "computer-readable medium" may include a single medium or multiple media, such as a centralized or distributed database, and/or associated caches and servers that store one or more sets of instructions. The term "computer-readable medium" may also include any medium that is capable of storing, encoding, or carrying a set of instructions for execution by a processor or that cause a computer system to perform any one or more of the methods or operations disclosed herein. The computer-readable medium 422 may be non-transitory, and may be tangible.

The computer-readable medium 422 can include a solid-state memory such as a memory card or other package that houses one or more non-volatile read-only memories. The computer-readable medium 422 can be a random-access memory or other volatile re-writable memory. Additionally or alternatively, the computer-readable medium 422 can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the disclosure is considered to include any one or more of a computer-readable medium or a distribution medium and other equivalents and successor media, in which data or instructions may be stored.

In an alternative implementation, dedicated hardware implementations, such as application specific integrated circuits, programmable logic arrays and other hardware devices, can be constructed to implement one or more of the methods described herein. Applications that may include the apparatus and systems of various implementations can broadly include a variety of electronic and computer systems. One or more implementations described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

The computer system 401 may be connected to a network 470. The network 470 may define one or more networks including wired or wireless networks. The wireless network may be a cellular telephone network, an 802.11, 802.16, 802.20, or WiMAX network. Further, such networks may include a public network, such as the Internet, a private network, such as an intranet, or combinations thereof, and may utilize a variety of networking protocols now available or later developed including, but not limited to TCP/IP based networking protocols. The network 470 may include wide area networks (WAN), such as the Internet, local area networks (LAN), campus area networks, metropolitan area networks, a direct connection such as through a Universal Serial Bus (USB) port, or any other networks that may allow for data communication. The network 470 may be configured to couple one computing device to another computing device to enable communication of data between the devices. The network 470 may generally be enabled to employ any form of machine-readable media for communicating information from one device to another. The network 470 may include communication methods by which information may travel between computing devices. The network 470 may be divided into sub-networks. The sub-networks may allow access to all of the other components connected thereto or the sub-networks may restrict access between the components. The network 470 may be regarded as a public or private network connection and may include, for example, a virtual private network or an encryption or other security mechanism employed over the public Internet, or the like.

In accordance with various implementations of the present disclosure, the methods described herein may be implemented by software programs executable by a computer system. Further, in an exemplary, non-limited implementation, implementations can include distributed processing, component/object distributed processing, and parallel processing. Alternatively, virtual computer system processing can be constructed to implement one or more of the methods or functionality as described herein.

The present disclosure furthermore relates to the following aspects.

ASPECTS

1. A computer-implemented method (100) for generating a personalized lecture for a user, comprising:
   obtaining (110) at least one time series of electrodermal activity data of a user from a sensor (12);
   identifying (120) a mental state of the user Based on the at least one time series of electrodermal activity data;
   obtaining (130) a teaching content; and
   generating (140) a personalized lecture based on the mental state and the teaching content.
2. The method (100) according to aspect 1, wherein obtaining (130) a teaching content comprises capturing at least one time series of audio data by a microphone (18).
3. The computer-implemented method (100) according to aspect 2, wherein the at least one microphone (18) is comprised within a writing instrument (10).
4. The method (100) according to any preceding aspect, wherein the at least one time series of electrodermal activity data is captured by the sensor (12) configured to measure the electric conductivity of skin.

5. The method (100) according to any preceding aspect wherein the sensor (12) is comprised within a writing instrument (10).

6. The method (100) according to any preceding aspect, wherein the at least one time series of electrodermal activity data comprises at least one time series of a skin conductance level and/or a skin conductance response.

7. The method (100) according to any preceding aspect, wherein obtaining the teaching content comprises a user, in particular the lecturer, entering the teaching content into a receiver.

8. The method (100) according to any preceding aspect, wherein the at least one time series of audio data is interpretable in terms of a natural language.

9. The method (100) according to any one of aspects 2 to 8, wherein the at least one time series of audio data is interpreted (150) into alphanumerical form, in particular string-form, to generate a time series of alphanumerical data.

10. The method (100) according to any preceding aspect, wherein obtaining the teaching content comprises a teaching content identification algorithm.

11. The method (100) according to any preceding aspect, wherein the teaching content identification algorithm comprises:
determination of at least one text module of the at least one time series of alphanumerical data, such as N-grams, in particular bi-grams, Noun phrases, themes and/or facets;
obtaining (130) the teaching content conveyed by comparing the at least one text module to predetermined text modules.

12. The computer-implemented method (100) according to aspect 11, wherein the predetermined text modules, are queried from a teaching content database.

13. The method (100) according to any preceding aspect, wherein generating (140) the personalized lecture comprises applying a personalized lecture content creation algorithm configured to generate a personalized lecture content based on the teaching content.

14. The method (100) according to aspect 13, wherein the personalized lecture content creation algorithm comprises querying a lecture content database based on the teaching content, in particular querying a lecture content database based on the teaching content to obtain data related to a teaching content.

15. The method (100) according to any aspect 13 or 14, wherein the personalized content creation algorithm comprises processing the teaching content or data related to a teaching content by an autoregressive language model, more specifically an autoregressive language model using deep learning, in particular a generative pre-trained transformer 3.

16. The method (100) according to any preceding aspect, wherein the personalized lecture comprises a personalized lecture audio sequence based on the personalized lecture content, in particular a personalized lecture audio sequence of a lecturer based on the personalized lecture content.

17. The method (100) according to aspect 16, wherein the personalized audio sequence is generated by a text to speech system, in particular a text to speech system using audio data of speech by the lecturer.

18. The method (100) according to any aspect 16 or 17, wherein the personalized audio sequence is based on the at least one time series of audio data or portions thereof.

19. The method (100) according to any preceding aspect, wherein the personalized lecture comprises a personalized lecture video sequence, wherein the personalized lecture video sequence comprises a mouth performing a series of mouth movements based on the personalized lecture audio sequence, in particular a mouth of the lecturer performing a series of mouth movements based on the personalized lecture audio sequence of the lecturer.

20. The method (100) according to aspect 19, wherein the personalized video sequence is generated by a neural network, more specifically a generative adversarial network framework, and in particular a generative adversarial network framework using one or more prior video sequences of the lecturer.

21. The method (100) according to aspect 19 or 20, wherein the series of mouth movements is generated by a neural network, more specifically a generative adversarial network framework and in particular a generative adversarial network framework using one or more prior video sequences of the lecturer.

22. The method (100) according to any one aspect 19 to 21, wherein the series of mouth movements is generated based on at least one prior series of mouth movements by a person, in particular the lecturer, in particular wherein the series of mouth movements is generated based on at least one prior series of mouth movements by a person, in particular the lecturer, and a related audio sequence expressed by the person.

23. The method (100) according to any one aspects 19 to 22, wherein the personalized lecture video sequence is based on a video recording of the lecturer, in particular a video recording of the lecturer captured at the same time as the at least one time series of audio data.

24. The method (100) according to any preceding aspect, wherein the at least one time series of electrodermal activity data is obtained by measuring a skin conductance in an interval between about 0.1 Hz to about 100 Hz, more specifically between about 1 Hz to about 20 Hz and in particular between about 1 Hz to about 10 Hz.

25. The method (100) according to any one of aspects 6 to 24, wherein the skin conductance level is the floating average of the skin conductance over a time period between about 10 s to about 60 minutes, more specifically between about 2 minute to about 20 minutes and in particular between about 5 minutes to about 10 minutes.

26. The method (100) according to any preceding aspect, wherein identifying (120) the user's mental state based on the at least one time series of electrodermal activity data comprises applying a mental state recognition algorithm.

27. The method (100) according to aspect 26, wherein the mental state recognition algorithm is configured to compare the one or more time series of electrodermal activity data, or one or more portions thereof, to one or more threshold values.

28. The method (100) according to aspect 26 or 27, wherein the mental state recognition algorithm comprises applying a through-to-peak technique and/or a continuous decomposition analysis on the at least one time series of electrodermal activity data.

29. The method (100) according to any one of aspects 26 to 28, wherein the mental state recognition algorithm is configured to compare the at least one time series of electrodermal activity data, or one or more portions thereof, to predetermined time series of electrodermal activity data related to predetermined mental states, or portions thereof.

30. The method (100) according to any one of aspects 26 to 29, wherein the mental state recognition algorithm comprises processing the at least one time series of electrodermal activity data by a neural network, in particular a neural network including one or more recurrent neural networks, more particularly a neural network including one or more long-short term memory neural network.

31. The method (100) according to any preceding aspect, wherein the mental state corresponds to at least one of a plurality of predefined mental states.

32. The method (100) according to any preceding aspect, wherein the identified (120) mental state may be an attentiveness, confidence, boredom, anxiety and/or sadness.

33. The method (100) according to any preceding aspect, wherein the identified (120) mental state is quantified, more specifically wherein the identified (120) mental state is ranked into tiers, and in particular wherein the identified (120) mental state is ranked into tiers from a low tier to a high tier.

34. The method (100) according to any preceding aspect, wherein a personalized lecture is generated (140) depending on the identified (120) mental state.

35. The method (100) according to any one of aspects 32 to 34, wherein the identified (120) mental state is a lack of attentiveness, in particular a low tier of attentiveness.

36. The method (100) according to any one of aspects 32 to 35, wherein the identified (120) mental state is a lack of confidence, in particular a low tier of confidence and/or wherein the identified mental state is a high degree of confidence, in particular a high tier of confidence.

37. The method (100) according to any preceding aspect, wherein an alertness signal is generated depending on the identified (120) mental state, more specifically when a lack of attentiveness is identified, in particular when a low tier of attentiveness is identified.

38. A computer system (300) configured to execute the computer-implemented method (100) according to any preceding aspect.

39. The computer system (300) of aspect 38, comprising:
a writing instrument (10) comprising:
a sensor (12) configured to measure the electric conductivity of skin;
a first interface (16);
a processing unit (20) remote from the writing instrument, comprising:
a second interface (22);
wherein the first (16) and second interface (20) are configured to exchange data.

40. The system (300) of aspect 39, wherein the first interface (16) is configured to send the at least one time series of electrodermal activity data to the second interface (22).

41. The system (300) of any one of aspects 39 to 40, wherein the second interface is configured to send a notification that a personalized lecture is available to the first interface (16).

42. A writing instrument (10) comprising:
a sensor (12) configured to measure the electric conductivity of skin;
a first interface (14) configured to communicate with a second interface (22).

43. The writing instrument according to aspect 42, wherein the writing instrument comprises a signaler, in particular a vibrating alert configured to activate when receiving the alertness signal.

44. A non-transitory computer-readable medium (400) characterized by a processor configured to execute the computer-implemented method (100) according to any one of aspects 1 to 37.

The invention claimed is:

1. A computer-implemented method for generating a personalized lecture video sequence for a user, comprising:
obtaining at least one time series of electrodermal activity data of the user from a sensor;
identifying a mental state of the user based on the at least one time series of the electrodermal activity data;
obtaining a teaching content; and
generating the personalized lecture video sequence based on the mental state and the teaching content, wherein the personalized lecture video sequence includes a person having generated mouth movements based on a related audio sequence, and further wherein the generated mouth movements are generated by a neural network trained on at least one prior series of real mouth movements by the person and a corresponding predetermined audio sequence.

2. The computer-implemented method of claim 1, wherein obtaining the teaching content comprises capturing at least one time series of audio data by a microphone.

3. The computer-implemented method of claim 2, wherein the at least one time series of the audio data is interpreted into alphanumerical form to generate a time series of alphanumerical data.

4. The computer-implemented method of claim 1, wherein the at least one time series of the electrodermal activity data is captured by the sensor configured to measure electric conductivity of skin.

5. The computer-implemented method of claim 1, wherein the sensor is comprised within a writing instrument.

6. The computer-implemented method of claim 1, wherein the at least one time series of the electrodermal activity data comprises at least one time series of a skin conductance level and/or a skin conductance response.

7. The computer-implemented method of claim 1, wherein obtaining the teaching content comprises a teaching content identification algorithm, wherein the teaching content identification algorithm comprises:
determining at least one text module of at least one time series of alphanumerical data, wherein the at least one time series of the alphanumerical data comprise N-grams, bi-grams, Noun phrases, themes and/or facets; and
obtaining the teaching content conveyed by comparing the at least one text module to predetermined text modules.

8. The computer-implemented method of claim 1, wherein the neural network comprises a generative adversarial network framework.

9. The computer-implemented method of claim 1, wherein identifying mental state of the user based on the at least one time series of the electrodermal activity data comprises applying a mental state recognition algorithm.

10. The computer-implemented method of claim 9, wherein the mental state recognition algorithm is implemented by a recurrent neural network that processes the at least one time series of electrodermal activity data, and wherein the mental state recognition algorithm processes the at least one series of electrodermal activity data by applying a trough-to-peak technique and/or a continuous decomposition analysis.

11. The computer-implemented method of claim 10, wherein the at least one time series of the electrodermal activity data comprises at least one time series of a skin conductance level, and wherein the skin conductance level is a floating average of the skin conductance over a time period between about 2 minutes to about 20 minutes.

12. The computer-implemented method of claim 11, wherein the identified mental state is ranked into at least one of a low tier or a high tier.

13. The computer-implemented method of claim 1, wherein an alertness signal is generated depending on the identified mental state.

14. The computer-implemented method of claim 1, wherein generating the personalized lecture comprises applying a personalized lecture content creation algorithm configured to generate a personalized lecture content based on the teaching content, wherein the personalized lecture content creation algorithm comprises querying a lecture content database based on the teaching content, in particular querying the lecture content database based on the teaching content to obtain data related to the teaching content, and wherein the personalized content creation algorithm comprises processing the teaching content or the data related to the teaching content by an autoregressive language model, wherein the autoregressive language model uses deep learning comprising a generative pre-trained transformer.

15. The computer-implemented method of claim 14, wherein the personalized lecture comprises a personalized lecture audio sequence based on the personalized lecture content, in particular a personalized lecture audio sequence of a lecturer based on the personalized lecture content.

16. A computer system for generating a personalized lecture video sequence for a user, comprising:
one or more processors; and
at least one non-transitory computer readable medium storing instructions which, when executed by the one or more processors, cause the one or more processors to perform operations comprising:
obtaining at least one time series of electrodermal activity data of the user from a sensor;
identifying a mental state of the user based on the at least one time series of the electrodermal activity data;
obtaining a teaching content; and
generating the personalized lecture video sequence based on the mental state and the teaching content, wherein the personalized lecture video sequence includes a person having generated mouth movements based on a related audio sequence, and further wherein the generated mouth movements are generated by a neural network trained on at least one prior series of real mouth movements by the person and a corresponding predetermined audio sequence.

17. The computer system of claim 16, comprising:
a writing instrument comprising:
the sensor configured to measure electric conductivity of skin; and
a first interface;
a processing unit remote from the writing instrument, comprising:
a second interface, wherein the first and second interface are configured to exchange data.

18. A writing instrument comprising:
a sensor configured to measure electric conductivity of skin;
a first interface configured to communicate and exchange data with a second interface of a processing unit, wherein the processing unit is configured to perform operations comprising:
obtaining at least one time series of electrodermal activity data of a user of the writing instrument from the sensor;
identifying a mental state of the user based on the at least one time series of the electrodermal activity data;
obtaining a teaching content; and
generating a personalized lecture video sequence based on the mental state and the teaching content, wherein the personalized lecture video sequence includes a person having generated mouth movements based on a related audio sequence, and further wherein the generated mouth movements are generated by a neural network trained on at least one prior series of real mouth movements by the person and a corresponding predetermined audio sequence.

19. The writing instrument of claim 18, wherein the writing instrument comprises a signaler, and wherein the signaler comprises a vibrating alert configured to activate upon receiving an alertness signal.

20. A non-transitory computer-readable medium for generating a personalized lecture video sequence for a user, the non-transitory computer-readable medium storing instructions which, when executed by one or more processors, cause the one or more processors to perform operations comprising:
obtaining at least one time series of electrodermal activity data of the user from a sensor;
identifying a mental state of the user based on the at least one time series of the electrodermal activity data;
obtaining a teaching content; and
generating the personalized lecture based on the mental state and the teaching content, wherein the personalized lecture video sequence includes a person having generated mouth movements based on a related audio sequence, and further wherein the generated mouth movements are generated by a neural network trained on at least one prior series of real mouth movements by the person and a corresponding predetermined audio sequence.

* * * * *